United States Patent
Roche del Ayala (10) Patent No.: US 8,147,471 B2
(45) Date of Patent: Apr. 3, 2012

(54) SANITARY NAPKIN WITH BRAID

(75) Inventor: Gabriela Roche del Ayala, Monterrey (MX)

(73) Assignee: Merimont US, Houston, TX (US)

( * ) Notice: Subject to any disclaimer, the term of this patent is extended or adjusted under 35 U.S.C. 154(b) by 357 days.

(21) Appl. No.: 12/440,920

(22) PCT Filed: Sep. 11, 2007

(86) PCT No.: PCT/US2007/078171
§ 371 (c)(1),
(2), (4) Date: Mar. 11, 2009

(87) PCT Pub. No.: WO2008/033846
PCT Pub. Date: Mar. 20, 2008

(65) Prior Publication Data
US 2009/0312729 A1    Dec. 17, 2009

Related U.S. Application Data (60) Provisional application No. 60/825,244, filed on Sep. 11, 2006.

(51) Int. Cl.
*A61F 13/15* (2006.01)
(52) U.S. Cl. .......... 604/385.17; 604/385.01; 604/385.03
(58) Field of Classification Search ............ 604/385.01, 604/385.03–385.05, 385.101, 385.17, 385.18
See application file for complete search history.

(56) References Cited

U.S. PATENT DOCUMENTS

| | | |
|---|---|---|
| 2,099,931 A | 11/1937 | Fourness |
| 2,401,284 A | 5/1946 | Winter et al. |
| 2,532,438 A | 12/1950 | Behr |
| 2,624,078 A | 1/1953 | Winter et al. |
| 3,101,714 A | 8/1963 | Penksa |
| 3,911,785 A | 10/1975 | Hood |
| 3,975,980 A | 8/1976 | Hood |
| 4,016,911 A | 4/1977 | Looker |
| 4,380,949 A | 4/1983 | Betta |
| 4,533,357 A | 8/1985 | Hall |
| 5,019,061 A | 5/1991 | Hodén et al. |
| 5,060,549 A | 10/1991 | Beal |
| 5,067,384 A | 11/1991 | Scala |
| 5,127,911 A | 7/1992 | Baharav |
| 5,169,394 A | 12/1992 | Jean |
| 5,458,589 A | 10/1995 | Comin-DuMong |
| 5,520,675 A * | 5/1996 | Knox-Sigh .............. 604/385.17 |
| 5,743,896 A | 4/1998 | Parker |
| 5,934,168 A | 8/1999 | Feichtinger et al. |
| 5,988,386 A | 11/1999 | Morrow |
| 6,059,763 A * | 5/2000 | Brown ...................... 604/385.17 |
| 6,142,984 A | 11/2000 | Brown et al. |
| 6,186,994 B1 * | 2/2001 | Bowles et al. ........... 604/385.17 |
| 6,206,867 B1 | 3/2001 | Osborn, III et al. |
| 6,258,075 B1 * | 7/2001 | Taylor et al. ............. 604/385.18 |
| 6,264,640 B1 * | 7/2001 | Sutton ...................... 604/385.18 |

(Continued)

FOREIGN PATENT DOCUMENTS

EP    1332744    8/2003

(Continued)

*Primary Examiner* — Lynne Anderson
(74) *Attorney, Agent, or Firm* — Baker & McKenzie LLP (57) ABSTRACT

The present invention relates to a sanitary napkin whose securing means includes a "braid" of absorbent material. The braid structure maximizes absorbency, while minimizing bulk and thus allows the pad to be comfortably held in place during use, in much the same way that the popular underwear are held.

19 Claims, 7 Drawing Sheets

U.S. PATENT DOCUMENTS

| | | | |
|---|---|---|---|
| 6,312,419 B1 | 11/2001 | Durel-Crain | |
| 6,613,031 B2 | 9/2003 | Glasgow et al. | |
| 6,676,649 B2 | 1/2004 | Mizutani | |
| 6,700,035 B2 | 3/2004 | Yoshimasa | |
| 6,821,270 B2 | 11/2004 | Rosenfeld | |
| 6,863,664 B2 * | 3/2005 | Wada et al. | 604/385.17 |
| 6,890,326 B2 * | 5/2005 | White | 604/385.17 |
| 6,997,915 B2 | 2/2006 | Gell et al. | |
| 7,056,312 B1 | 6/2006 | Metcalf | |
| 7,147,628 B2 | 12/2006 | Drevik | |
| 7,196,241 B2 | 3/2007 | Kinoshita et al. | |
| 7,235,708 B2 | 6/2007 | Guidotti et al. | |
| 2001/0011169 A1 | 8/2001 | Taylor et al. | |
| 2002/0133133 A1 | 9/2002 | Agyapong et al. | |
| 2003/0191443 A1 | 10/2003 | Taylor et al. | |
| 2005/0229770 A1 | 10/2005 | Smeets et al. | |
| 2005/0277088 A1 | 12/2005 | Fischer et al. | |
| 2006/0030828 A1 | 2/2006 | Wilhelm et al. | |
| 2006/0206089 A1 * | 9/2006 | Coley | 604/385.17 |
| 2006/0282059 A1 | 12/2006 | Fujikawa et al. | |
| 2008/0077105 A1 * | 3/2008 | Hooi | 604/385.17 |

FOREIGN PATENT DOCUMENTS

| | | |
|---|---|---|
| WO | WO 9004956 | 5/1990 |

* cited by examiner

| Experiment | Weight of Pad in Original Packaging | Weight of Wet Pad With Braid | Weight of Wet Pad Without Braid | Percentage Increase Due to Braid |
|---|---|---|---|---|
| 1 | .3 oz | 1.9 oz | 1.7 oz | 20% |
| 2 | .3 oz | 2 oz | 1.4 oz | 40% |
| 3 | .3 oz | 1.5 oz | 1.4 oz | 10% |

FIG. 8

SANITARY NAPKIN WITH BRAID

CROSS-REFERENCE TO RELATED APPLICATIONS

This application is a 35 U.S.C. Section 371 of PCT/US2007/078171 filed Sep. 11, 2007, which claims priority to U.S. Provisional Application 60/825,244 filed Sep. 11, 2006, both incorporated herein by reference in their entirety.

FEDERALLY SPONSORED RESEARCH STATEMENT

Not applicable.

REFERENCE TO MICROFICHE APPENDIX

Not applicable.

FIELD OF THE INVENTION

The invention relates to sanitary napkins improved with an extending braid, to be worn like a thong. The braid provides much improved absorbency protection and fit, and yet is comfortable to wear.

BACKGROUND OF THE INVENTION

The effectiveness of external feminine sanitary protection products such as sanitary napkins depends upon a good fit, which serves to minimize discomfort and provide the maximum absorbent surface area. However, despite the importance of fit to sanitary protection, most prior art napkins are secured either by adhesion to an undergarment or rely on the use of belts, safety pins or clips and other attachment means. Typically the undergarment itself doesn't fit well, and even if it does, nothing prevents the pad from bunching and minimizing the absorbent surface area. Further, the adhesives often fail, and the pad shifts and fails in its primary task. Belts provide greater security, but they are bulky, restrictive, uncomfortable, and few women use them.

A variety of sanitary products have employed some type of projection to assist in either or both of fluid absorption and fit. U.S. Pat. No. 7,056,312 describes a sanitary napkin with an absorbent tab disposed at an obtuse angle to the napkin body. U.S. Pat. No. 6,997,915 describes a pad including a substantially planar strip adapted to be received between the buttocks of the wearer to thereby help hold the pad in place. U.S. Pat. No. 5,127,911 describes a sanitary napkin with a string that, when pulled, draws together the longitudinal edges of the napkin and forms a contoured projection. U.S. Pat. No. 5,169,394 describes a sanitary napkin having an elongated absorbing member whereby one end is slidably attached to the pad to allow adjustment of the fit. U.S. Pat. No. 4,533,357 describes napkin having a flexible tab portion shaped to comfortably fit between the buttocks of the wearer. U.S. Pat. No. 5,743,896 describes a sanitary napkin having a protrusion insertable between the buttocks of a wearer. EP1332744 describes a sanitary napkin with a gluteal groove strip. U.S. Pat. No. 6,613,031 describes a sanitary napkin having a tail strip extending rearwardly, again to fit between the buttocks. Finally, WO9004956 describes a sanitary napkin having an absorbent stub piece, again to fit between the buttocks.

However, each of these suffers from the same disadvantage, in that the protrusion is either too bulky for comfort, or if sufficiently slender for comfort, then it lacks sufficient absorbency. What is needed in the art is a napkin that is both comfortable and sufficiently absorbent.

SUMMARY OF THE INVENTION

The invention provides a sanitary napkin which achieves a dynamic body fit because the pad is securely held in place by a braid positioned toward the middle of the pad. An intergluteal strip or "braid" of absorbent material maximizes absorbency, while minimizing bulk. The braid allows the pad to be comfortably held in place during use, in much the same way that the popular thong underwear are held, and provides a secure yet comfortable fit. Further, the braid has superior absorbency and improves the functioning of the pad.

Figure 1:
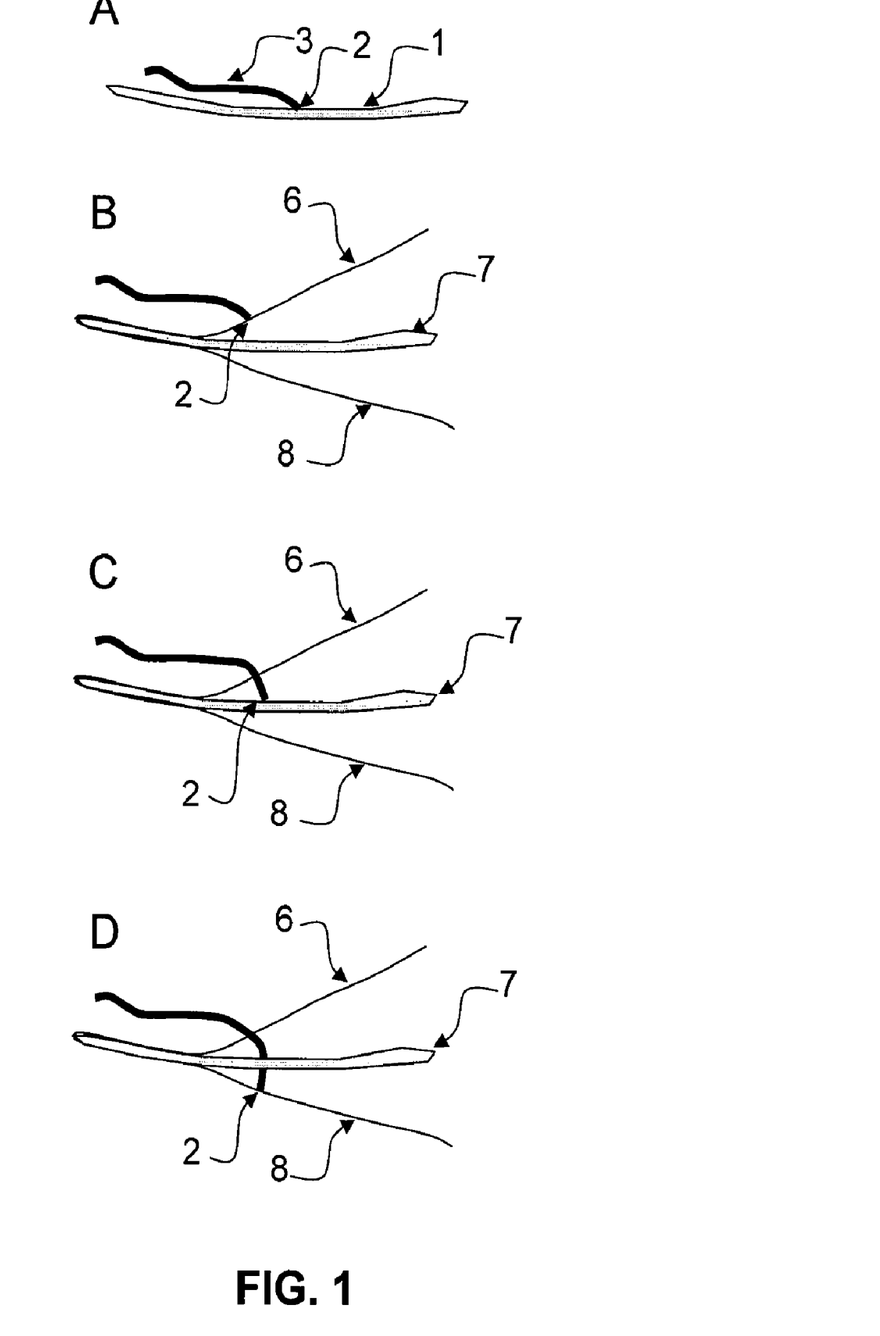
FIG. 1A-D. Side view showing a braid secured to the pad.

In one embodiment, the sanitary napkin has a pad body having an elongated shape and having an absorbent core between an inner liner and a outer liner. There may also be a barrier layer that may be integral with the outer liner or may be a separate layer, and the sanitary napkin can also include wings and/or adhesives. An elongated braid extends upwardly from the pad body, generally positioned centrally or in the back half of the pad body. The braid is made of at least three strands of braided fiber and is absorbent. The braid can be made from two or more different fibers, one of which is absorbent, and can include cotton. The braid can be a diamond braid having a hollow core and an absorbent material filling the hollow core, or can be a solid braid. The braid can be stitched, glued, melted, welded or otherwise adhered to the pad body (FIG. 1). It can be stitched to the outer liner of the pad body (8) and protrude through the absorbent core and inner liner, it can be attached to the absorbent core (7) or it can be attached to the inner liner of the pad body (6).

A "sanitary pad" or "sanitary napkin" is a disposable absorbent pad used to absorb urine, uterine flow during menstruation, post surgery fluids, and post partum fluids. Sanitary pads may also be referred to as an adult diaper, incontinence pad, post surgical diaper, post partum diaper, maximum absorbency pad or sanitary napkin. The sanitary pad has an inner surface, a core, and an outer surface. The "inner" surface is closest the skin of the wearer and the "outer" surface touches the wearers clothing.

By "braid" or "braided" what is meant is that one or more separate strands of material are knitted, braided, plaited or woven to form a series of "interlocking loops." This provides maximum strength and absorbency, while minimizing bulk.

Braiding is well known in the art, and any braid pattern may be used, including the simple tri-strand braid commonly used to braid hair. However, a locking braid can be used where it is contemplated that the user will trim the braid length for best fit. In a preferred embodiment, the braid forms a hollow tube, which can then be filled with an extremely absorbent core material or super-absorbent material. In other embodiments, at least two different kinds of fibers are used to make the braid, the first fiber selected for absorbency and the second fiber selected for strength. Thus the composite braid will exhibit the best of both features without sacrificing either. In yet another preferred embodiment, the braid will include stretchable fibers, and thus the braid itself will be stretchable.

Fibers may be constructed of natural, manufactured, synthetic or blended materials. Fibers may be fabrics, threads, yarns or other formed materials. Natural materials include, but are not limited to, cotton, hemp, wool, wood-pulp or other natural materials. Manufactured fibers like cellulose may be processed to increase absorbency or change the texture of the material. Synthetic materials may include polyacrylate, polypropylene, polyester, polyethylene, polyurethane, and LYCRA®. In one embodiment a super-absorbent is incorporated into the material. In another embodiment a wicking material is incorporated to facilitate the movement of moisture.

Examples of suitable braiding are described in U.S. Pat. No. 3,911,785, U.S. Pat. No. 3,975,980, U.S. Pat. No. 4,016,911, U.S. Pat. No. 4,380,949, U.S. Pat. No. 5,067,384, U.S. Pat. No. 5,060,549, US2005229770, US2005277088, and the like.

DESCRIPTION OF EMBODIMENTS OF THE INVENTION

The invention is generally directed to an improved hygienic pad that incorporates a braided tail or stem to eliminate leakage, even on heavy flow days. The braid is worn between the buttocks, in a manner similar to that seen with a thong bikini. The braid is configured to be soft, flexible, and will shape itself to a woman's anatomy. In some embodiments, the braid can taper from the thickest point at or near the pad body to the thinnest point at the end of the braid. The braid structure allows it to have sufficient strength, even when of minimal size, thus ensuring an enduring fit. Further, with the proper selection of materials, both strength and absorbency can be achieved without incurring bulk and thus sacrificing comfort. In some embodiments, the braid ranges from 10 to 30 cm in length, preferably it is from 15-25 cm, and most preferably the braid is left long enough for the wearer to trim to comfort.

The pad is made in any manner known in the art. The reader is referred to napkin art and copious diaper art for teachings on the construction of absorbent articles including U.S. Pat. No. 7,235,708, U.S. Pat. No. 7,196,241, U.S. Pat. No. 7,147,628, U.S. Pat. No. 6,821,270 and U.S. Pat. No. 6,676,649. In a preferred embodiment, the pad includes an inner dry lining, an absorbent core, and an outer barrier layer. The pad may also include a second outer lining for improved aesthetics, especially when the pad is made as a disposable panty/pad. In a preferred embodiment, the pad materials will be biodegradable.

Standard sanitary napkins have a inner or top sheet, core, and outer or bottom sheet. Standard inner sheet materials can be inexpensive, nonwoven topsheet or sophisticated three-dimensional films that provide a unidirectional moisture barrier. Core materials directly affect pad size and absorbency. Acquisition layers, fluff pulp, and airlaid cores can be used to increase absorbency. Standard fluff requires more material to achieve the same absorbency as high-density fluff mixed with super absorbent polymer (SAP) granule powder. SAP is a white powder that not only absorbs moisture instantaneously upon contact, but also holds that moisture securely. Some super absorbent powders can absorb 400 to 1,000 times their own weight in pure water, or 30 to 70 times their own weight in urine. Fluff layers with integrated SAP powder can provide up to 60% cost savings for raw material, increasing absorbency while decreasing bulk and cost. In one embodiment the SAP can be polyacrylate polymers with a variety of crosslinking and associated salts including sodium polyacrylate, microporous cellulose, carbohydrate acrylic copolymer, or other highly absorbent material. Ultrathin cores, with or without binders, provide a number of fluff layers with an integrated SAP powder. One or more intermediary acquisition layers between the topsheet and core materials may be used to provide additional protection and absorbency. Customized sanitary napkins include tri-fold, single wrapping, with or without wings, and thong pantyliners with an attached waist.

The pad can be any shaped designed for comfort, which typically includes generally oval, rectangular, triangular, hour-glass, and variations thereof with somewhat concave sides. Size can vary according to flow, with heavy flow requiring a longer and/or thicker pad. Size may also be adjusted also according to a woman's size, including petite or junior sizes that are correspondingly smaller than a woman's pad. The pad may be any length and in one embodiment pads range from 10 to 50 cm lengths. The pad may also be 10, 15, 20, 25, 30, 35, 40, 45 or 50 cm in length. Wings may be added to the sides of the pad, as well as adhesives to the bottom and/or wings that secure the pad to an undergarment.

Figure 2:
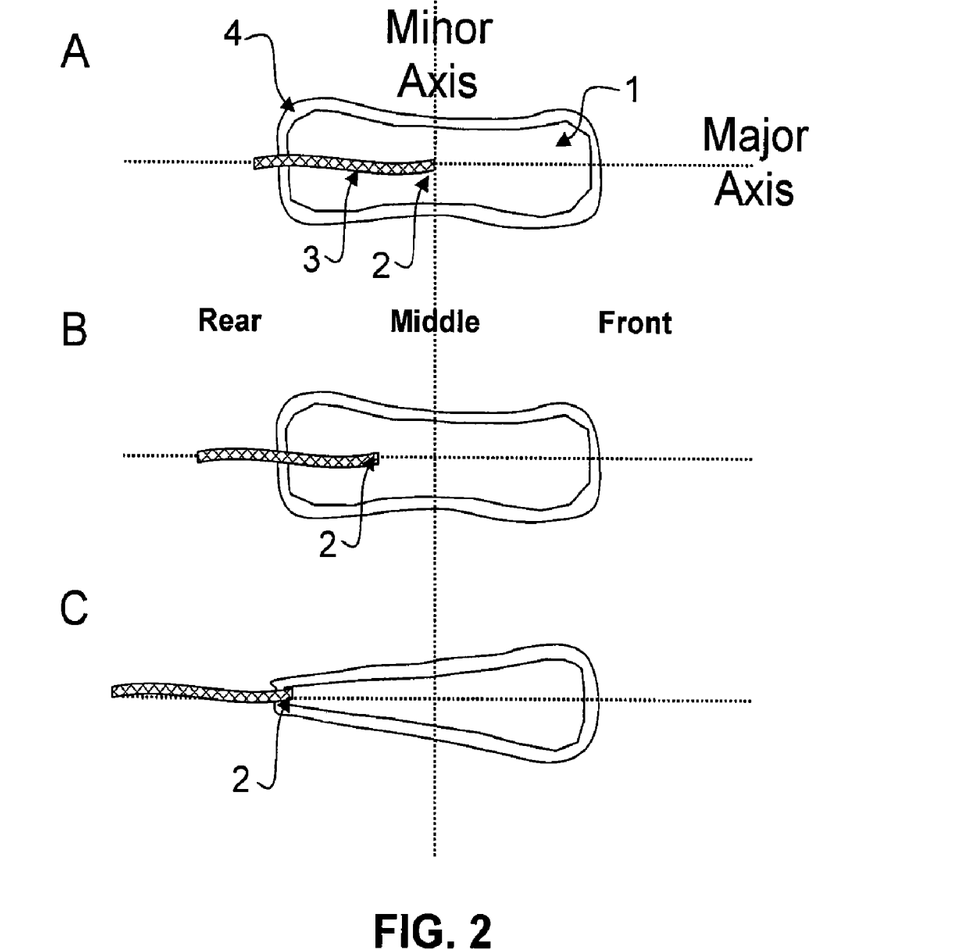
FIG. 2. Top view showing major and minor axis. The braid (3) is attached (2) to the pad (1) along the major axis from the median (A) to the rear of the pad (C). The pad may be tapered (C) for a more comfortable fit. A outer barrier can be created by sewing or binding the pad to create a ridge (4).

The braid should be attached at or near the midpoint of the minor axis of the pad, its exact position along the major axis depends on the shape and length of the pad. Thus, in a thong-like underwear or pad (FIG. 2C), the braid can be more rearward, but in the traditional rectangular pad it can be centrally located along both axis (FIG. 2A), although it can also tend towards the back half of the major axis of the pad (FIG. 2B). In one embodiment the braid is placed in the middle of the minor and major axes as shown in FIG. 2A. In another embodiment the braid is placed in the center of the minor axis and 3-5 cm from the rear of the major axis. In another embodiment the braid is placed at 1, 2, 3, 4, 5, 6, 7, 8, 9, 10, 11, 12, 13, 14, or 15 cm from the rear of the major axis. The braid may also be placed a portion of the distance from the rear of the major axis. The braid may be placed ½ or midway along the major axis (FIG. 2A), thus the braid is in the exact middle of the pad. The braid may also be placed at ⅓ of the total length, thus the braid would be placed at 10 cm on a 30 cm pad or at 5 cm on a 15 cm pad. The braid may also be placed at ¼, ⅕, ⅖, ⅙, ⅐, 2/7, 3/7, ⅛, ⅜, or ⅝ the total distance from the rear of the pad.

The braid can be used without any attachment means but may also be attached to the wearer or an undergarment. Adhesives can be used on the outer surface of the braid, or to the end of the braid, allowing secure attachment to either the wearer or the undergarment. Alternatively, the braid can attach to an elastic waistband, or may include an attachment means (such as Velcro or a hook), allowing it to feed over the wearer's thong back and attach to itself.

The braid will be attached to the pad in any manner known in the art. The braid may be attached to the inner liner (FIG. 1B), absorbent core (FIG. 1C), or outer liner (FIG. 1D), thus protruding through the inner liner. In a preferred embodiment, the braid is attached to the pad by stitching or adhesive or heat. In the preferred embodiment, the threads comprising the braid are pressed into the pad body forming "roots" approximately two centimeters in length through the inner liner and into the pad, and may be unbraided or braided in this area. In an alternate embodiment, the braid is woven integrally with a woven liner layer.

Braid fibers can be made of a variety of materials, including natural fibers such as cotton, hemp, linen, paper, and combinations thereof, while absorbent core materials include fluff pulp, dried hydrogel (such as sodium polyacrylate, sodium acrylate, potassium acrylate, or an alkyl acrylate), and the like. In the preferred embodiment, the braid fibers will be made from cotton. The fibers may also be impregnated with a variety of polymers to improve their absorbency. Absorbency is measured in accordance with the methods described in U.S. Pat. No. 6,700,035 (incorporated herein by reference in its entirety), which describes infiltration, diffusivity and liquid returnability under pressure tests. In the preferred embodiment, the braid fibers will be lined or impregnated with a synthetic material that will aid in absorption.

Pads are seen as hygiene products—merely functional products devoid of aesthetic qualities. In contrast, in its most preferred embodiment, this product will be both appealing and feminine. It will be manufactured in a variety of colors, scented and embossed or printed with various designs. Between the materials, the colors, the designs and the scents, this pad will be like attaching a charming sticker to your underwear.

The pad of the invention is exemplified in the following examples. However, the examples are illustrative only, and are not to be construed as limiting.

EXAMPLE 1

Pad Structure

Figure 3:
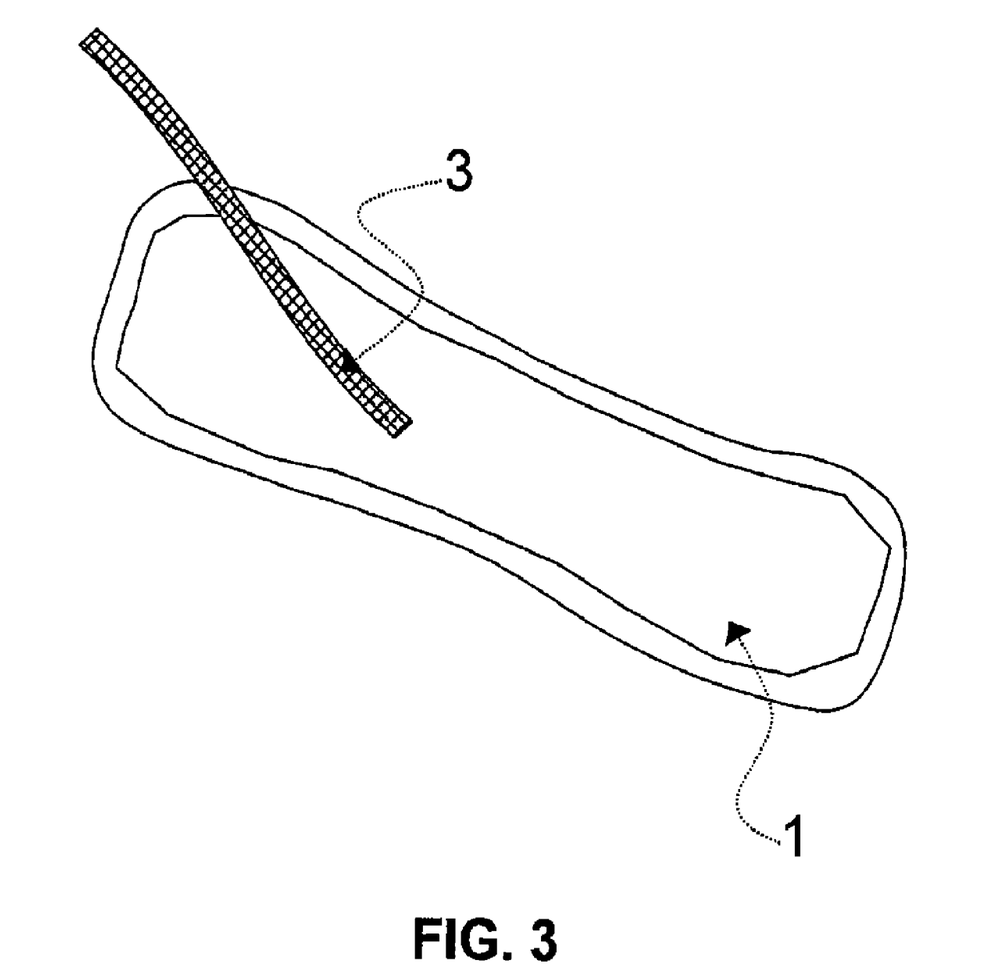
FIG. 3. Perspective View.
Figure 4:
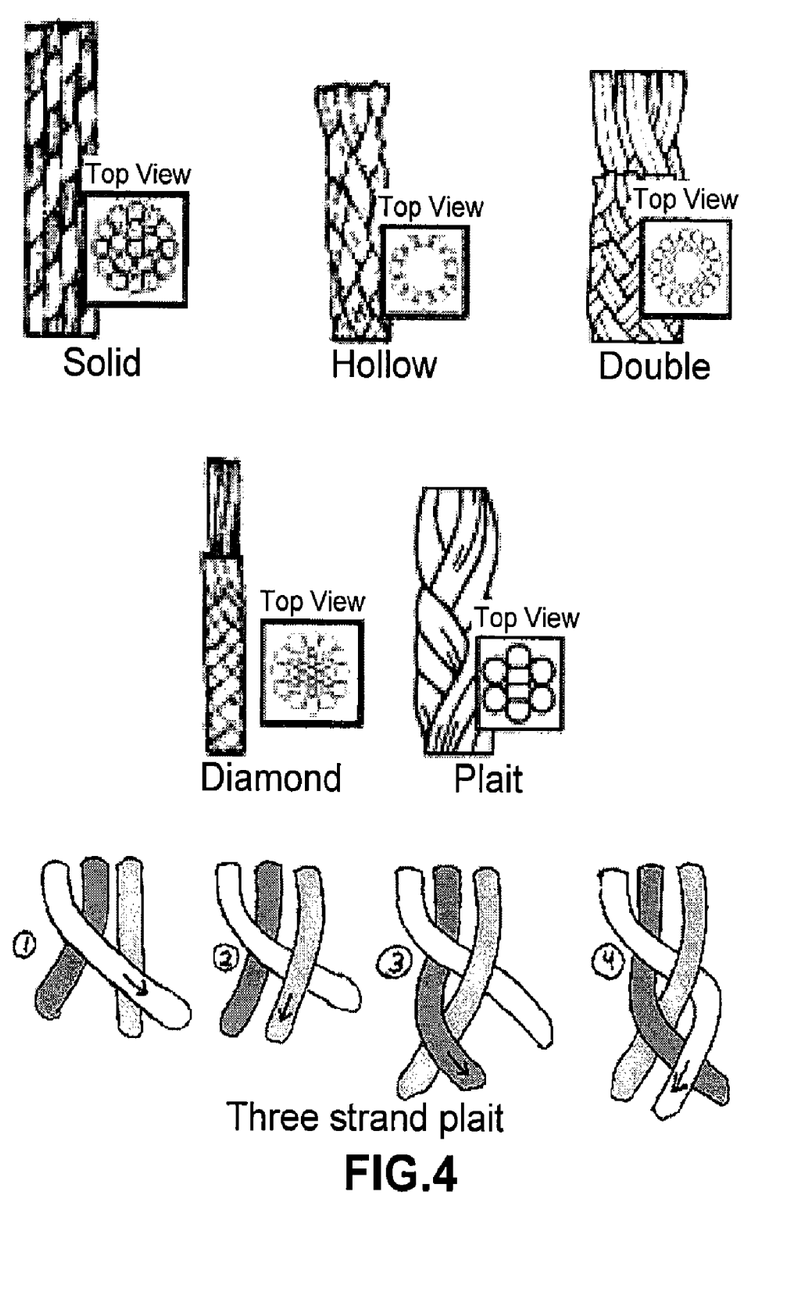
FIG. 4. Various braid styles demonstrating Solid, Hollow, Double, Diamond, and Plait braids. Braiding of a simple three strand plait is shown.

FIG. 1A shows a side view of the pad (1), illustrating the braid (3) attached to the pad (2) roughly in the center of the elongated pad. FIG. 1B-D demonstrate attachment to the inner liner (6), the absorbent core (7) and the outer liner (8). FIG. 2A shows a top view of the inner side of the pad with the braid (3) attached in the middle of the pad (2). FIG. 2B shows the braid attached in the rear portion of the pad. FIG. 2C shows a braid attached to the end of a "thong" shaped pad. FIG. 3 shows a perspective view.

EXAMPLE 2

Pad Manufacture

In one embodiment, the pad of the invention is manufactured using a sanitary napkin pad, and incontinence pad machine. Production can easily run a wide range of raw materials and produce sanitary napkins with various manufacturing structures because the machine has been designed to assure simple and rapid size changes. In one embodiment, ultrathin cores with binders provide a number of fluff layers with an integrated SAP powder layered with non-woven air-laid transition layers. Braided attachments are incorporated with adhesive on the topsheet prior to folding, stacking and packing. Thong pantyliners with a 180 degree turn are woven directly into the braided string. After the braid is incorporated, the napkins enter a tri-folding, stacking and packing unit, which completes the production process.

EXAMPLE 3

Ultrasonic Sealing

The braided attachment can be added after the sanitary napkin or incontinence pad is assembled. In one embodiment, a braid with three threads made of cotton and lined with a man-made absorbent material are sewn or sealed by ultrasound to the inner liner of the absorbent pad. The cotton braid is pressed using a press at 7000 kg for 15 minutes. The braid is placed in the middle of the sanitary napkin. In one embodiment using a 24-cm sanitary napkin the braid is placed at 12 cm. The braid was fixed to the sanitary napkin using ultrasound. Briefly, the braid is unwound at one end to create "roots" about 2 cm long inside the sanitary napkin through the inner liner and into the absorbent pad. The un-braided "roots" are heated by ultrasound and adhered to the inner liner leaving the "roots" embedded in the absorbent pad. In one embodiment the braid is 12 cm long. In a preferred embodiment the braid is 15 cm long. A loose braid can be used to keep the material soft and pliable. A tighter braid makes the material more stiff, thus care must be taken to control the tightness of the weave and ensure the braid is comfortable. In another embodiment the braid could be tapered from thicker to thinner allowing for maximum absorbance and comfort.

EXAMPLE 3

Pad Underwear

Figure 5:
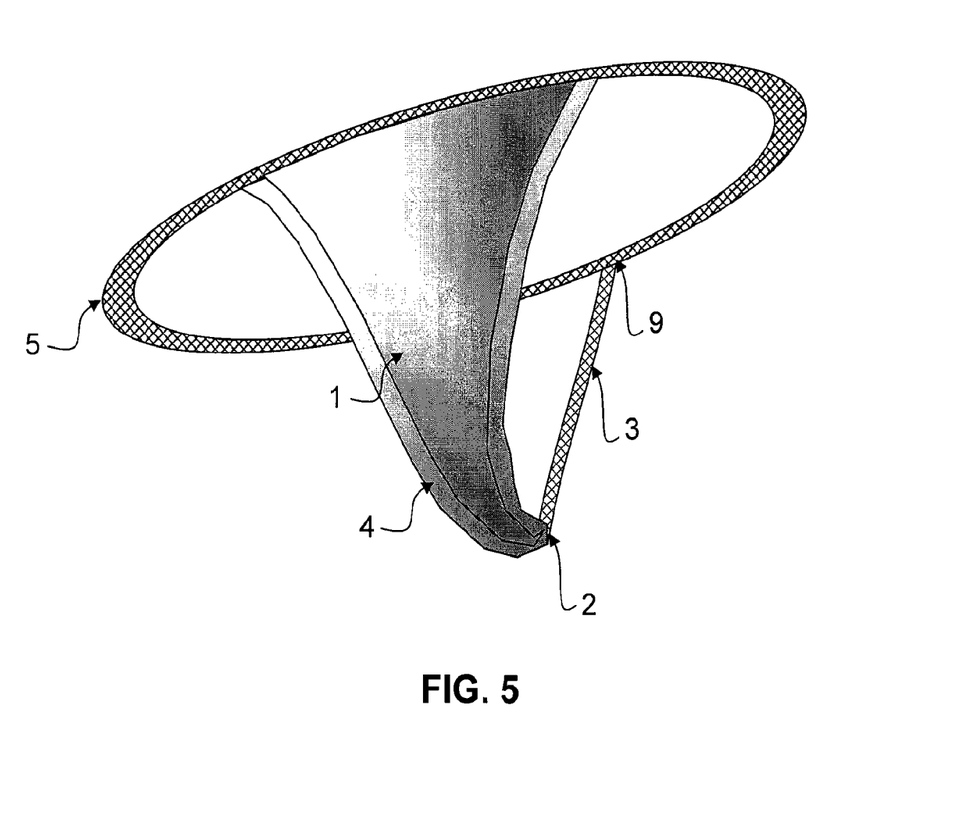
FIG. 5. A disposable sanitary pad and thong underwear is demonstrated. The pad (1) is attached (2) to the braid (3) which can then be either formed integrally with or attached at 90° (9) to a (circular) waistband (5).
Figure 6A:
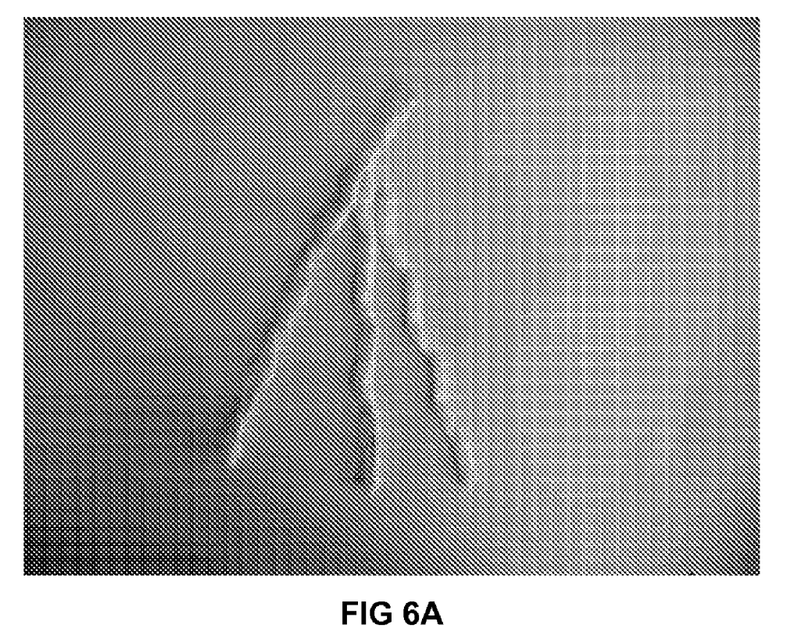
FIG. 6A-B. Close up of exemplary braid structure with large braid near the pad, and a smaller or thinner braid at the opposite end.
Figure 6B:
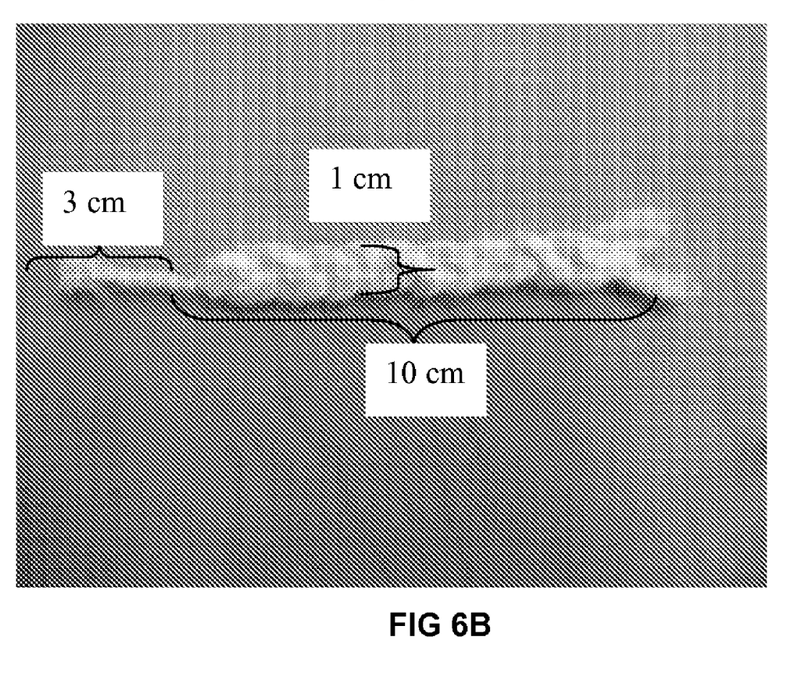
Figure 7:
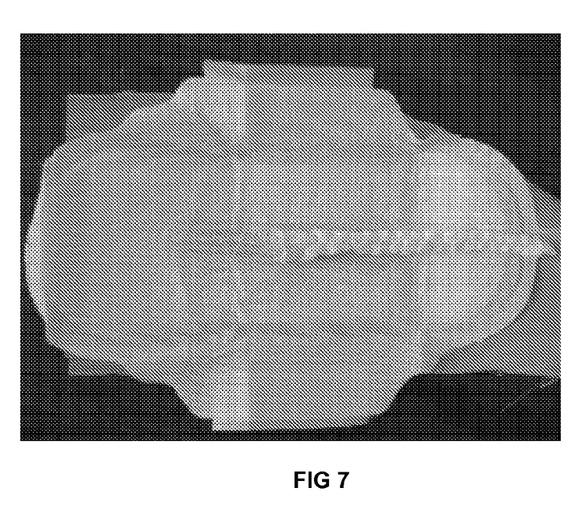
FIG. 7. Photograph of exemplary embodiment.
Figure 8:
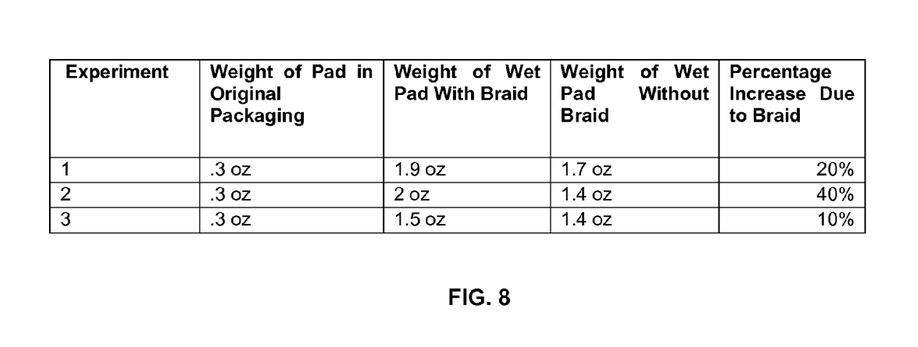
FIG. 8. Table showing increased absorbency contributed by braid of 10-40%. Pad weighed with the braid attached; placed under running water for ten seconds, drained for an additional ten seconds and weighed with and without braid.

In another embodiment, the pad is configured to provide an entire disposable thong underwear (FIG. 5). The braid (3) terminates in a stretch waistband (5), and the front of the pad is elongated, flared and connected to the waistband 5. In this instance, the pad (1) is broader in the front, and tapers towards the braid, thus providing a comfortable, yet disposable underwear and pad combination. In this configuration, the outer surface of the pad is chosen to be aesthetically pleasing and comfortable to wear, but inexpensive to manufacture. In another embodiment the braid is elongated to form the waistband. A strip of Velcro®, adhesive or loops along the front edge of the pad allows attachment to the waistband at varying configurations. The braid can be a single length up to 100 cm with an adjustable clip at the end for connection at the 90° turn (9) allowing the wearer to customize the length of the braid. In another embodiment a second braid is attached somewhere along the first braid forming a "Y" or "T" back the wearer can then attach both braids to the front of the pad making a custom waistline. The attachment means can be any suitable structure, including hooks and loops, adhesives, snaps, clips and the like, or can be a permanent attachment, rather than a removable attachment means, in which case, the braids can be highly elasticized to accommodate a variety of sizes.

All citations referenced herein are incorporated by reference in their entirety.

1. U.S. Pat. No. 3,911,785, H. A. Hood, "Parallel yarn rope."
2. U.S. Pat. No. 3,975,980, H. A. Hood, "Method and apparatus for manufacturing faired article."
3. U.S. Pat. No. 4,016,911, R. Looker, "Woven rope."
4. U.S. Pat. No. 4,380,949, W. Betta, "Braided stranded rope forming machine."
5. U.S. Pat. No. 4,533,357, F. E. Hall, "Sanitary napkin construction."
6. U.S. Pat. No. 5,060,549, M. Beal, "Safety rope for climbing and manufacturing method therefor."

7. U.S. Pat. No. 5,067,384, E. Scala, "Braider method and apparatus for manufactured faired rope or cable."
8. U.S. Pat. No. 5,127,911, E. Baharav, "Sanitary feminine napkin with a mechanism for optional contouring."
9. U.S. Pat. No. 5,169,394, L. D. Jean, "Feminine sanitary napkin."
10. U.S. Pat. No. 5,743,896, B. M. Parker, "Sanitary napkin having a protrusion insertable into the posterior rugae of the buttocks."
11. U.S. Pat. No. 6,613,031, Glasgow, et al., "Sanitary napkin with intergluteal strip."
12. U.S. Pat. No. 6,676,649, S. Mizutani, "Sanitary napkin having upper and lower absorbent cores."
13. U.S. Pat. No. 6,700,035, Y. Wataru, "Absorbent article."
14. U.S. Pat. No. 6,821,270, L. G. Rosenfeld, "Sanitary absorbent article."
15. U.S. Pat. No. 6,997,915, Gell, et al., "Sanitary napkin with adjustable length intergluteal strip."
16. U.S. Pat. No. 7,056,312, R. L. Metcalft, "Sanitary napkin with absorbent tab."
17. U.S. Pat. No. 7,147,628, S. Drevik, "Absorbent article with improved liquid handling ability."
18. U.S. Pat. No. 7,196,241, Kinoshita, et al., "Sanitary napkins with compressed grooves."
19. U.S. Pat. No. 7,235,708, Guidotti, et al. "Absorbent article comprising an absorbent structure."
20. US2005229770, Smeets, et al., "Endless rope."
21. US2005277088, D. E. Fischer, "Reinforced gingival retraction cord."
22. EP 1332744, Glasgow, et al., "Sanitary napkin with intergluteal strip."
23. WO9004956, B. C. Muller, "Sanitary napkin."

What is claimed is:

1. A sanitary pad, comprising:
 a) a pad body having an elongated shape with a major axis and a minor axis and comprising an inner liner above an absorbent core above an outer liner; and
 b) an elongated braid attached to said pad body about mid way along the minor axis, wherein said braid comprises at least three strands of braided fiber and is absorbent, wherein the braid is a diamond braid having a hollow core and having an absorbent material filling the hollow core.

2. The sanitary pad of claim 1, wherein the strands of fiber are selected from the group consisting of cotton, hemp, wool, wood-pulp, cellulose, polyacrylate, polypropylene, polyester, polyethylene, polyurethane, LYCRA® and combinations thereof.

3. The sanitary pad of claim 1, wherein the braid is made from two different fibers, one of which is absorbent.

4. The sanitary pad of claim 1, wherein at least one of the fibers is cotton.

5. The sanitary pad of claim 1, wherein the absorbent material is selected from the group consisting of a super absorbent polymer, polyacrylic acid, polyacrylamide copolymer, ethylene maleic anhydride copolymer, cross-linked carboxy-methyl-cellulose, polyvinyl alcohol copolymers, cross-linked polyethylene oxide, sodium polyacrylate, microporous cellulose, carbohydrate acrylic copolymer, and starch grafted copolymer.

6. The sanitary pad of claim 1, wherein the braid tapers from a thick portion near the pad body to a thin portion away from the pad body.

7. The sanitary pad of claim 1, wherein the braid is attached to the pad body at the intersection of the major and minor axes.

8. The sanitary pad of claim 1, wherein the braid is attached to the pad body along the major axis between the rear of the pad and the intersection of the major and minor axes.

9. The sanitary pad of claim 1, wherein the braid further comprises an unbraided portion of thread that is attached to the pad body.

10. The sanitary pad of claim 1, wherein the braid is stitched to the pad body.

11. The sanitary pad of claim 1, wherein the braid is adhered to the pad body.

12. The sanitary pad of claim 1, wherein the braid is attached to the outer liner of the pad body and protrudes through the absorbent core and inner liner.

13. The sanitary pad of claim 1, wherein the braid is attached to the absorbent core of the pad body and protrudes through the inner liner.

14. The sanitary pad of claim 1, wherein the braid is attached to the inner liner of the pad body.

15. The sanitary pad of claim 1, wherein the braid is 10-30 centimeters in length.

16. The sanitary pad of claim 1, wherein the outer liner is imprinted with designs, and the pad body is impregnated with perfume.

17. The sanitary pad of claim 1, wherein the outer liner is a color other than white.

18. A sanitary pad comprising an elongated pad body having a major and minor axis, said elongated pad body having an absorbent core, and a braid attached to said elongated pad body at about the mid point of the minor axis and between the rear of the elongated pad body and the intersection of the major and minor axes, said braid comprising at least three braided fibers and an absorbent material and being greater than 10 cm in length, wherein the braid is a diamond braid having a hollow core and having an absorbent material filling the hollow core.

19. An improved sanitary pad having a pad body, the improvement comprising a braid attached to the pad body and positioned to fit intergluteally and comprising at least three braided fibers and an absorbent material, wherein the braid is a diamond braid having a hollow core and having an absorbent material filling the hollow core.

* * * * *